US 6,616,655 B1

(12) United States Patent
Falwell et al.

(10) Patent No.: US 6,616,655 B1
(45) Date of Patent: Sep. 9, 2003

(54) METHOD AND APPARATUS FOR PERFORMING CARDIAC ABLATIONS

(75) Inventors: Gary S. Falwell, Manchester, NH (US); Donald Patterson, North Chelmsford, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/325,230

(22) Filed: Jun. 3, 1999

(51) Int. Cl.$^7$ ................................................ A61B 18/18
(52) U.S. Cl. .......................... 606/41; 606/49; 607/101
(58) Field of Search .......................... 606/41, 45, 49, 606/50; 607/101, 102, 122

(56) References Cited

U.S. PATENT DOCUMENTS

| | | | |
|---|---|---|---|
| 4,444,206 A | * | 4/1984 | Gold |
| 5,005,587 A | | 4/1991 | Scott .......................... 128/786 |
| 5,156,151 A | | 10/1992 | Imran |
| 5,277,201 A | | 1/1994 | Stern |
| 5,281,213 A | | 1/1994 | Milder et al. ................. 606/15 |
| 5,370,644 A | | 12/1994 | Langberg ..................... 606/33 |
| 5,403,311 A | * | 4/1995 | Abele et al. .................. 606/49 |
| 5,462,527 A | | 10/1995 | Stevens-Wright et al. .... 604/95 |
| 5,643,197 A | | 7/1997 | Brucker et al. ............... 604/20 |
| 5,653,684 A | * | 8/1997 | Laptewicz et al. ............ 604/22 |
| 5,860,974 A | | 1/1999 | Abele |
| 5,891,136 A | | 4/1999 | McGee et al. |
| 5,913,854 A | * | 6/1999 | Maguire et al. ............... 606/41 |
| 5,913,856 A | * | 6/1999 | Chia et al. ..................... 606/41 |
| 5,919,188 A | * | 7/1999 | Shearon et al. ............... 606/41 |
| 5,944,715 A | * | 8/1999 | Goble et al. .................. 606/41 |
| 6,006,123 A | * | 12/1999 | Nguyen et al. ............ 600/374 |
| 6,522,930 B1 | * | 2/2003 | Schaer et al. ............... 607/101 |

FOREIGN PATENT DOCUMENTS

| | | |
|---|---|---|
| EP | 0 428 279 B1 | 1/1997 |
| WO | WO 99/22659 | 5/1999 |

OTHER PUBLICATIONS

McRury, et al., Circulation, 96:4057–4064, 1997.

* cited by examiner

Primary Examiner—Roy D. Gibson
(74) Attorney, Agent, or Firm—Darby & Darby

(57) ABSTRACT

A novel device and method for performing cardiac ablations includes a therapeutic instrument, for example, an ablation catheter, to which is mounted a flexible, braided electrode. The electrode configuration is selected so that it has a desired surface area for proper heat convection properties. RF energy is delivered to the electrode to heat and thereby ablate local heart tissue, with the electrode having good convection abilities to protect against coagulation, embolisms, and other undesirable effects of ablation procedures.

18 Claims, 2 Drawing Sheets

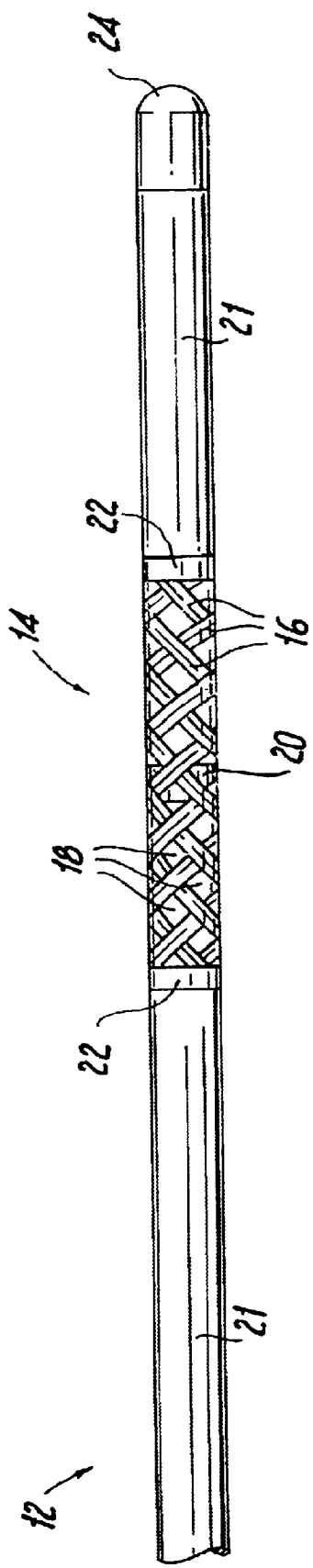
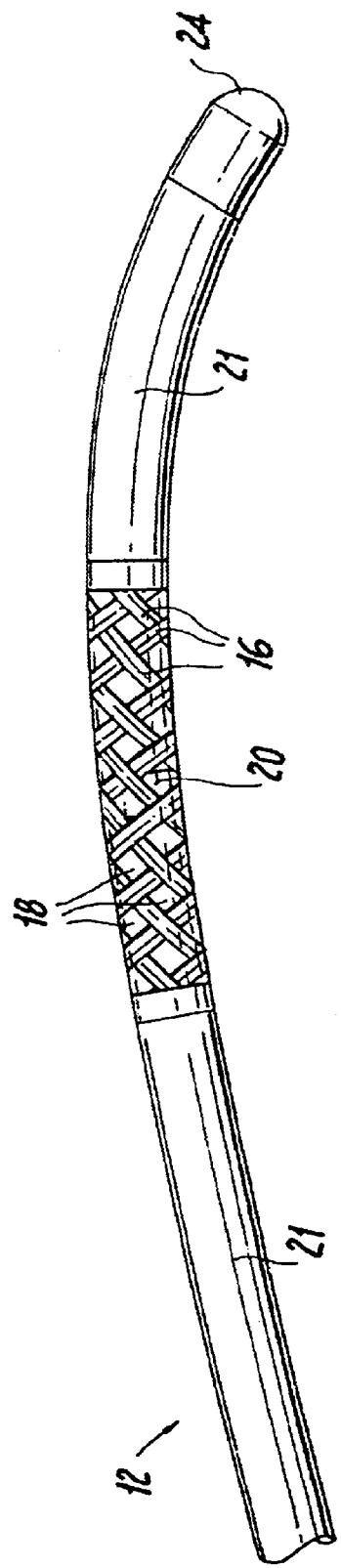
FIG. 2
FIG. 3

METHOD AND APPARATUS FOR PERFORMING CARDIAC ABLATIONS

FIELD OF THE INVENTION

The present invention generally relates to the field of cardiac ablation. More specifically, the invention is directed to a method and system for performing cardiac ablations while minimizing the risk of adverse effects such as blood coagulation and the attendant risk of an embolism.

BACKGROUND OF THE INVENTION

Cardiac arrhythmias, commonly known as irregular heart beats or racing hearts, are the result of various physical defects in the heart itself. One such defect is an extraneous strand of muscle fiber in the heart that provides an abnormal short-circuit pathway for electric impulses traveling through the heart tissue. This accessory pathway often causes the electric impulses that normally travel from the upper to the lower chamber of the heart to be fed back to the upper chamber, causing the heart to beat irregularly and therefore inefficiently pump blood.

Another common type of cardiac arrhythmia is ventricular tachycardia (VT), which may be a complication resulting from a heart attack or from a temporary reduction of blood supply to an area of heart muscle. VT is often caused by a tiny lesion, typically on the order of one to two millimeter, that is located close to the inner surface of the heart chamber. That lesion is often referred to as an "active site", because it does not fire in sequence with the rest of the heart muscle. VT causes the heart's normal rhythmic contraction to be altered, thereby affecting heart function. A typical symptom is rapid, inefficient heart beats.

Minimally invasive techniques have been developed which are used to locate cardiac regions responsible for the cardiac arrhythmia, and also to disable the short-circuit function of these areas. According to these techniques, electrical energy shocks are applied to a portion of the heart tissue to ablate that tissue and produce scars which interrupt the reentrant conduction pathways. The regions to be ablated are usually first determined by endocardial mapping techniques. Mapping typically involves the percutaneous introduction of a diagnostic catheter having one or more electrodes into the patient, passing the diagnostic catheter through a blood vessel. (e.g. the femoral vein or aorta) and into an endocardial site (e.g., the atrium or ventricle of the heart), and inducing a tachycardia so that a continuous, simultaneous recording can be made with a multichannel recorder at each of several different endocardial positions. When a tachycardia focus is located, as indicated in the electrocardiogram recording, it is marked by means of a fluoroscopic image so that cardiac arrhythmias at the located site can be ablated. An ablation catheter with one or more electrodes can then provide electrical energy to the tissue adjacent the electrode to create a lesion in the tissue. One or more suitably positioned lesions will create a region of necrotic tissue to disable the malfunction caused by the tachycardia focus.

Ablation is carried out by applying energy to the catheter electrodes once the electrodes are in contact with the cardiac tissue. The energy can be, for example, RF, DC, ultrasound, microwave, or laser radiation. When RF energy is delivered between the distal tip of a standard electrode catheter and a backplate, there is a localized RF heating effect. This creates a well-defined, discrete lesion slightly larger than the tip electrode (i.e., the "damage range" for the electrode), and also causes the temperature of the tissue in contact with the electrode to rise.

Often, to overcome cardiac arrhythmias such as atrial flutter and atrial fibrillation, it is necessary to create a long, continuous lesion (i.e., a linear lesion). However, in order to maintain sufficient flexibility in the catheter shaft so that it may bend and assume requisite configurations to establish proper tissue contact, the conventional ring electrodes mounted on ablation catheters must be kept relatively short. Thus, to form a long, continuous lesion, clinicians have been forced to perform what is commonly referred to as a "drag" method, in which an ablation electrode is dragged along the patient's tissue while ablation energy is delivered to the electrode to scar the adjacent tissue to create a lesion. Such methods suffer from a number of disadvantages. For example, once the portion of the catheter shaft carrying the ablation electrode is making good tissue contact, it is undesirable to move the catheter shaft, because of the risk of losing the tissue contact. In addition, if the electrode is dragged too quickly, the tissue will not be sufficiently heated to scar.

Others have attempted to overcome this problem by incorporating a relatively long, cylindrical electrode mounted over the catheter shaft. The relatively long electrode can create longer lesions without requiring that the electrode (and thus the catheter shaft) be moved. However, using long electrodes also has significant drawbacks, one being that an elongated electrode detracts from the flexibility of the catheter, such that the catheter may not be able to assume a desired curve due to the straightening effects of the elongated electrode(s).

Accordingly, it will be apparent that there continues to be a need for a device for performing ablations which facilitates the creation of linear lesions. In addition, there exists the need for a device which does not require the surgeon to physically drag the catheter shaft to create a linear lesion. The instant invention addresses these needs.

SUMMARY OF THE INVENTION

Briefly, the present invention provides a flexible, ablative element which is relatively long while still maintaining its flexibility. The ablative element in preferably in the form of a braided electrode comprising one or more interlaced, flexible, electrically conductive filaments. The ends of the braid are secured to respective ends of catheter shaft segments or the like. The filaments comprising the braided electrode are preferably selected to be substantially as flexible as the catheter shaft segments, and therefore can be made relatively long without detracting from the flexibility of the medical device itself.

In one embodiment, a ring electrode is provided and is connected to the inside surface of the braided electrode. The ring electrode preferably mounts thereon one or more temperature sensors which serve to monitor the temperature adjacent the electrode/tissue interface.

Thus, in one illustrative embodiment, the present invention is directed to a medical device including: a catheter including an elongated shaft that is insertable through a patient's vasculature; a braided electrode connected to the catheter at a predetermined location, the braided electrode comprising a plurality of intertwined, conductive members; and a source of energy connected to the catheter and in electrical communication with the conductive members of the braided electrode.

DESCRIPTION OF THE DRAWINGS

Other objects, features and advantages of the invention discussed in the above summary of the invention will be more clearly understood from the following detailed description of preferred embodiments, which are illustrative only, when taken together with the accompanying drawings in which:

FIG. 2 is a side view of the flexible, braided electrode shown in FIG. 1; and

FIG. 3 is a side view of the flexible, braided electrode manipulated to assume a curved configuration.

DETAILED DESCRIPTION OF THE PREFERRED EMBODIMENTS

Figure 1:
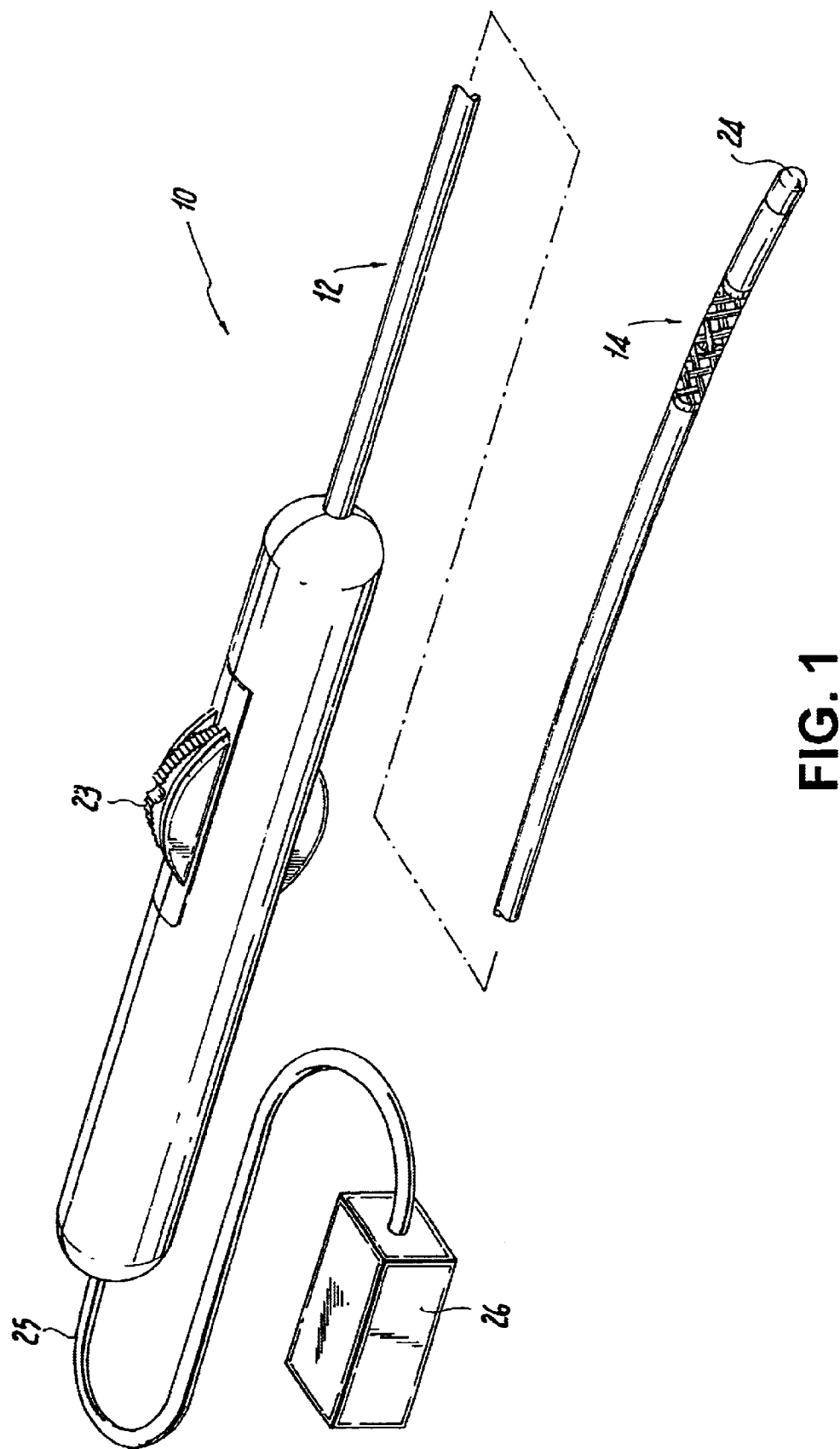
FIG. 1 is a perspective view of a medical device carrying a flexible, braided electrode illustrating one embodiment of the present invention.

Referring now to the drawings, and particularly to FIG. 1, there is shown a medical device 10 according to one illustrative embodiment of the present invention. The medical device 10 is operative to create relatively long, continuous lesions without requiring that a clinician physically drag the catheter within the patient or perform any other such manipulation. The medical device includes an elongated, flexible shaft 12 which may be manipulated through a patient's vasculature and to an intended site within the patient, for example, an active site which must be ablated. The medical device further includes an elongated, braided electrode 14 connected to the shaft at a predetermined location, the braided electrode being flexible so that it may bend with the shaft. Thus, the braided electrode may be made relatively long without causing the medical device to lose its flexibility.

The flexible shaft 12 may be a solid wire or hollow, and also may be formed of electrically conductive material. The shaft may comprise a guide wire, catheter shaft, or any other suitable device which is flexible for manipulation through a patient's vasculature to an intended site within the patient. In one illustrative embodiment, the shaft is part of a steerable catheter, which is steerable to facilitate manipulation thereof through the patient's vasculature, as is well known in the art.

The braided electrode 14 is preferably in the form of a plurality of interlaced, electrically conductive filaments 16. The filaments are flexible and capable of assuming various bent configurations to impart a curve to the medical device 10. The filaments are preferably formed of metallic elements having relatively small cross-sectional diameters, such that the filaments are resilient and can be biased to flex and thereby assume a curved configuration. When the bias is removed, the electrode preferably resumes its generally straight configuration, without permanent strain to the individual filaments. By providing a relatively large number of filaments, the electrode will have sufficient strength, thereby allowing for the inclusion of smaller, and therefore more strain-resistant, filaments. In one preferred embodiment, the filaments are formed of Nitinol®, but may be formed of gold, platinum, platinum-tungsten alloy, stainless steel, or any other suitable material, depending on the thermal conductivity characteristics desired for a particular application. Alternatively, the electrode may include nonmetallic elements woven with metallic elements, with the nonmetallic elements providing strain resistance to support the metallic elements that provide the ablative abilities.

In one illustrative embodiment, the openings (or "pixels") 18 defined between the respective filaments are of a preselected size and spacing such that the pixel density is on the order of approximately 10 to 60 pixels per linear inch. With such a construction, the electrode provides a high surface area electrode, which is efficient in convecting heat away from an ablation site, which is beneficial in creating good lesions. In addition, the braided electrode protects against blood coagulation and embolisms, which can result when ablating with a solid ring electrode, as is known in the art.

It will be understood that the dimensions of the filaments 16 and the pixel density and opening size can be selected based upon the particular application. In situations where a high degree of flexibility is required so that the electrode may assume curved configurations with small radii, the pixel density is relatively high and the pixel size is relatively small. Conversely, when a high degree of flexibility is not required, the pixel density may be relatively low.

In one illustrative embodiment, the filaments 16 are formed of an electrically conductive wire with a diameter of between about 0.001 and 0.010 inches. The filaments may be interwoven in a single-ended, two-over-two pattern, a double-ended, two-over-two pattern, or any other suitable woven pattern. Preferably, the braid pattern is from a single-ended two-over-two to an eight-ended two-over-two weave.

While the filaments 16 have been described as being cylindrical, the filaments may alternatively be formed of flat wire which permits bending relative to the plane defined by the flat wire. The flat wire is preferably selected having a thickness to width ratio of 1:2 to 5:8. In other words, the thickness is preferably between about 1 to 5 units, while the width is between about 2 to 8 units. The preferable braid patterns for the flat wire embodiment are the same as those for the cylindrical wire embodiment, as described above.

In one illustrative embodiment, the flexible shaft 12 is remotely controlled in a control handle at the proximal end of the device 10. One suitable form of handle is disclosed in U.S. Pat. No. 5,462,527 to Stevens-Wright, the disclosure of which is hereby expressly incorporated by reference as if fully set forth herein. As described in the patent, such a handle includes a rotatable thumb wheel 23 which is axially displaceable relative to the handle. The slide actuator is preferably connected to a pull wire (not shown), which extends along the length of the shaft 12 and connects to the shaft adjacent the distal end of the shaft at an off-axis location. Thus, the slide actuator may be displaced relative to the handle to tension the pull wire and thereby impart a curve to the shaft 12, as is well known in the art. With the shaft being curved, the electrode 14 also curves and may therefore be manipulated to assume a desired curve to complement the contour of a patient's anatomy. Another suitable form of control handle is disclosed in U.S. Pat. No. 5,611,777 to Bowden et al., which is also expressly incorporated herein by reference.

In one illustrative embodiment, the medical device 10 further includes a ring electrode 20 mounted to the inside of the braided electrode 14 at a generally central location thereon. Preferably, the ring electrode is connected to the braided electrode by means of a conductive adhesive to establish electrical communication between the two.

The ring electrode 20 preferably includes one or more temperature sensors (not shown) to sense the temperature adjacent the electrode/tissue interface. The temperature sensors are connected to respective conductive wires (not shown) which extend through the inside of the shaft and connect to suitable processing circuitry to determine the temperature being sensed, as is well known in the art.

The braided electrode 14 is preferably connected to the shaft by means of a pair of adhesive fillets 22 which connect the respective ends of the braided electrode to the shaft. According to that embodiment, the shaft 12 comprises a pair of shaft segments 21, with the electrode 14 interposed between the segments.

In one illustrative embodiment, the medical device 10 further includes a tip electrode 24 disposed at the distal end of the shaft 12, which may be used for diagnostic and/or therapeutic functions, as is known in the art.

The structure of the braided electrode 14 provides a number of advantages and benefits. Firstly, the braided electrode provides torque to the catheter in both directions, which adds stability to the device 10. In addition, the braided electrode provides a relatively large surface area for purposes of conductivity due to the fact that the braided electrode is essentially overlapping double helices. In addition, the surface area of the braided electrode can be increased while maintaining the flexibility of the braid by increasing the pixel density, which also changes the braiding angle (i.e., the angle approaches perpendicularity relative to the longitudinal axis).

In operation, the medical device 10 is advanced through the patient's vasculature to the intended site of interest, for example, to tissue within an atria. The clinician may then impart a bend to the distal portion of the shaft 12, and therefore to the braided electrode 14, by rotating the thumb wheel in the control handle, or in any other suitable manner. The curved electrode 14 may then be driven into contact with the patient's tissue, with the curve complementing the contour of the tissue to establish contact along at least a substantial portion of the length of the electrode.

The braided electrode 14 may also be used to create long, substantially linear lesions as well. The electrode is simply delivered to the appropriate site and brought into contact with the patient's tissue, without imparting a bend to the distal portion of the device 10.

In any event, once, the electrode is in the proper position, RF energy is delivered to the, electrode through a suitable conductive wire 25 or the like which leads from a source of electrical energy 26, for example, an RF generator or the like. The tissue then heats up and scars, thereby creating a lesion.

From the foregoing, it will be apparent to those skilled in the art that the present invention provides a medical device which is operative to create relatively long, continuous lesions without requiring that a clinician perform a drag procedure or the like.

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A medical device comprising:
   an elongated shaft that is insertable through a patient's vasculature;
   a braided electrode mounted on the shaft at a location spaced at a predetermined distance from the distal end of the shaft, the braided electrode comprising a plurality of intertwined, conductive members and defining a plurality of pixels, wherein the electrode includes between about 10 and about 60 pixels per linear inch, and the braided electrode overlying a section of the shaft that has a substantially continuous, uninterrupted surface; and
   a source of energy in electrical communication with the conductive members of the braided electrode.

2. The medical device of claim 1, wherein the conductive members are formed of one of gold, stainless steel, platinum, platinum-tungsten alloy, and Nitinol®.

3. The medical device of claim 1, wherein the braided electrode is formed by one of a single-ended, two-over-two pattern and a double-ended, two-over-two pattern.

4. The medical device of claim 1, further including a ring electrode connected to the braided electrode, the ring electrode carrying at least one temperature sensor.

5. The medical device of claim 1, wherein the braided electrode comprises a plurality of cylindrical wires having a diameter of between 0.001 and 0.010 inches.

6. The medical device of claim 1, wherein the braided electrode comprises a plurality of flat wires.

7. A method for performing cardiac ablation, comprising:
   manipulating a medical instrument to a desired location within a patient's body, the instrument comprising a flexible, braided electrode mounted on the shaft at a location spaced at a predetermined distance from the distal end of the instrument and defining a plurality of pixels, wherein the electrode includes between about 10 and about 60 pixels per linear inch, and
   the braided electrode overlying a section of the shaft that has a substantially continuous, uninterrupted surface;
   placing at least a portion of the electrode into contact with the patient's tissue; and
   delivering ablative energy to the electrode to ablate the patient's tissue.

8. The method of claim 7, wherein the step of manipulating comprises steering the medical instrument with a pull wire.

9. A medical device comprising:
   a catheter including an elongated shaft that is insertable through a patient's vasculature;
   a braided electrode mounted on the catheter at a location spaced at a predetermined distance from the distal end of the catheter, the braided electrode comprising a plurality of intertwined, conductive filaments and defining a plurality of pixels, wherein the electrode includes between about 10 and about 60 pixels per linear inch, and the braided electrode overlying an outer catheter surface that is substantially continuous and uninterrupted; and
   a source of energy connected to the catheter and in electrical communication with the conductive members of the braided electrode.

10. The medical device of claim 9, wherein the conductors are formed of one of gold, stainless steel, platinum, platinum-tungsten alloy, and Nitinol®.

11. The medical device of claim 9, wherein the braided electrode is formed by one of a single-ended, two-over-two pattern and a double-ended, two-over-two pattern.

12. The medical device of claim 9, further including a ring electrode connected to the braided electrode, the ring electrode carrying at least one temperature sensor.

13. The medical device of claim 9, wherein the braided electrode comprises a plurality of cylindrical wires having a diameter of between 0.001 and 0.010 inches.

14. A method for performing cardiac ablation, comprising:
   manipulating a medical instrument to a desired location within a patient's body, the instrument comprising a flexible, braided electrode mounted on the shaft at a location spaced at a predetermined distance from the distal end of the instrument and defining a plurality of pixels, wherein the electrode includes between about 10 and about 60 pixels per linear inch, and the braided electrode overlying a section of the shaft that has a substantially continuous, uninterrupted surface;

placing at least a portion of the electrode in a non-deployed state into contact with the patient's tissue; and delivering ablative energy to the electrode to ablate the patient's tissue.

15. A medical device comprising:

an elongated outer shaft adapted to contact tissue that is insertable through a patient's vasculature;

a braided electrode mounted on the outer shaft at a location spaced at a predetermined distance from the distal end of the outer shaft, the braided electrode comprising a plurality of intertwined, conductive members and defining a plurality of pixels, wherein the electrode includes between about 10 and about 60 pixels per linear inch, and the braided electrode overlying a section of the outer shaft that has a substantially continuous, uninterrupted surface; and a source of energy in electrical communication with the conductive members of the braided electrode.

16. A method for performing cardiac ablation, comprising:

manipulating a medical instrument to a desired location within a patient's body, the instrument comprising a flexible, braided electrode mounted on an outer shaft at a location spaced at a predetermined distance from the distal end of the instrument and defining a plurality of pixels, wherein the electrode includes between about 10 and about 60 pixels per linear inch, and the braided electrode overlying a section of the outer shaft that has a substantially continuous, uninterrupted surface, the outer shaft being adapted to contact a patient's tissue;

placing at least a portion of the electrode into contact with the patient's tissue; and delivering ablative energy to the electrode to ablate the patient's tissue.

17. A medical device comprising:

an elongated shaft that is insertable through a patient's vasculature;

a braided electrode mounted on the shaft at a location spaced at a predetermined distance from the distal end of the shaft, the braided electrode comprising a plurality of intertwined, conductive members and including a selected, curved configuration to complement the contour of a patient's tissue, the braided electrode overlying a section of the shaft that has a substantially continuous, uninterrupted surface; and a source of energy in electrical communication with the conductive members of the braided electrode.

18. A method for performing cardiac ablation, comprising:

manipulating a medical instrument to a desired location within a patient's body, the instrument comprising a flexible, braided electrode;

manipulating the electrode into a selected, curved configuration to complement the contour of a patient's tissue;

placing at least a portion of the electrode into contact with the patient's tissue; and delivering ablative energy to the electrode to ablate the patient's tissue.

* * * * *